United States Patent
Gibson et al.

(10) Patent No.: US 9,858,328 B2
(45) Date of Patent: Jan. 2, 2018

(54) DATA TAGGING

(71) Applicant: Verily Life Sciences LLC, Mountain View, CA (US)

(72) Inventors: David Andrew Gibson, Mountain View, CA (US); Mark Murphy, Palo Alto, CA (US)

(73) Assignee: Verily Life Sciences, LLC, South San Francisco, CA (US)

( * ) Notice: Subject to any disclaimer, the term of this patent is extended or adjusted under 35 U.S.C. 154(b) by 504 days.

(21) Appl. No.: 14/334,126

(22) Filed: Jul. 17, 2014

(65) Prior Publication Data

US 2016/0019283 A1    Jan. 21, 2016

(51) Int. Cl.
G06F 17/30    (2006.01)
G06F 19/00    (2011.01)

(52) U.S. Cl.
CPC ...... *G06F 17/30598* (2013.01); *G06F 19/322* (2013.01)

(58) Field of Classification Search
CPC .......................... G06F 17/30598; G06F 19/322
See application file for complete search history.

(56) References Cited

U.S. PATENT DOCUMENTS

| | | | |
|---|---|---|---|
| 7,214,190 B1 | 5/2007 | Wilson | |
| 7,701,580 B2 | 4/2010 | Bssler et al. | |
| 7,763,856 B2 | 7/2010 | Kiesel et al. | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 8,079,953 B2 * | 12/2011 | Braun | G06F 19/3406 128/920 |
| 8,153,949 B2 | 4/2012 | Kiesel et al. | |
| 8,323,188 B2 | 12/2012 | Tran | |
| 8,344,731 B2 | 1/2013 | Lee | |
| 8,368,402 B2 | 2/2013 | Lee et al. | |

(Continued)

FOREIGN PATENT DOCUMENTS

WO    0130231 A2    5/2001
WO    2013012862 A1    1/2013

OTHER PUBLICATIONS

Manuel Arruebo, Mónica Valladares, and África González-Fernández, Antibody-Conjugated Nanoparticles for Biomedical Applications, Journal of Nanomaterials, vol. 2009 (2009), Article ID 439389, 24 pages (available at http://dx.doi.org/10.1155/2009/439389).

(Continued)

*Primary Examiner* — Jay Morrison
(74) *Attorney, Agent, or Firm* — Kilpatrick Townsend & Stockton LLP

(57) ABSTRACT

A method for tagging and organizing data is provided. In one example, physiological data detected from a wearer of a wearable device is received and associated with a tag based, at least in art, on an input by the wearer. The input may be a state of the wearer, such as physical or mental state, or a rule. The collected physiological data may be organized based on the tag and, in some examples, on other types of received data, such as a wearer's personal data. In other example methods, data may be stored in a database based on one or more tags associated with the data.

26 Claims, 5 Drawing Sheets

(56) References Cited

U.S. PATENT DOCUMENTS

| | | |
|---|---|---|
| 8,398,546 B2 | 3/2013 | Pacione |
| 2004/0259270 A1 | 12/2004 | Wolf |
| 2005/0054907 A1 | 3/2005 | Page et al. |
| 2007/0255122 A1 | 11/2007 | Vol et al. |
| 2010/0049010 A1 | 2/2010 | Goldreich |
| 2011/0028803 A1 | 2/2011 | Ollmar |
| 2011/0029472 A1* | 2/2011 | Lai .................. G06N 5/025 706/47 |
| 2011/0117028 A1 | 5/2011 | Zharov |
| 2012/0047136 A1 | 2/2012 | Stergiou |
| 2012/0059664 A1* | 3/2012 | Georgiev ............ A61B 5/02 705/2 |
| 2012/0110082 A1* | 5/2012 | Brown ............ G06F 17/30731 709/204 |
| 2012/0165638 A1* | 6/2012 | Duke ............ A61B 5/14532 600/365 |
| 2013/0053990 A1 | 2/2013 | Ackland |
| 2013/0080843 A1* | 3/2013 | Stergiou .......... G06F 11/14 714/49 |
| 2013/0106684 A1* | 5/2013 | Weast ............ G06F 19/3481 345/156 |
| 2013/0274635 A1 | 10/2013 | Coza |
| 2014/0104075 A1 | 4/2014 | Ellis |
| 2014/0156646 A1* | 6/2014 | Brust ............ G06F 17/30554 707/722 |
| 2014/0180595 A1* | 6/2014 | Brumback ........... A61B 5/0015 702/19 |
| 2014/0197946 A1* | 7/2014 | Park ................ G08B 21/18 340/539.11 |
| 2014/0379369 A1* | 12/2014 | Kokovidis ........... A61B 5/002 705/2 |

OTHER PUBLICATIONS

Shao et al, "Magnetic nanoparticles for biomedical NMR-based diagnostics," Beilstein Journal of Nanotechnology, 2010, 1, 142-154.

Liu et al, "Magnetic resonance monitoring of focused ultrasound/magnetic nanoparticle targeting delivery of therapeutic agents to the brain," PNAS Early Edition, 2010, pp. 1-6.

* cited by examiner

DATA TAGGING

BACKGROUND

Unless otherwise indicated herein, the materials described in this section are not prior art to the claims in this application and are not admitted to be prior art by inclusion in this section.

A number of scientific methods have been developed in the medical field to evaluate a person's health state. A person's health state may, for example, be evaluated based on the measurement of one or more physiological parameters, such as blood pressure, pulse rate, skin temperature, or galvanic skin response (GSR). In a typical scenario, these measurements may be taken in the home or a health-care setting by using several discreet devices or sensors and, in some cases, by drawing blood or other bodily fluid. For most people, the measurements or blood tests are performed infrequently, and changes in a physiological parameter, which may be relevant to health state, may not be identified, if at all, until the next measurement is performed.

In another example, these parameters may be more frequently or continuously measured, and other health-related information obtained, by a wearable device. The device, which may be provided as a wrist-mounted device, may include one or more sensors for detecting or measuring one or more physiological parameters. For example, a wrist-mounted device may include optical sensors for heart rate and blood oxygen saturation ($SpO_2$) monitoring, a thermistor for measuring skin temperature, and a GSR sensor for measuring skin resistance. At least some of the physiological parameter information may be obtained by detecting the presence, absence and/or concentration of one or more analytes in the body. The wearable device may further include or be in communication with other sensors such as accelerometers, inertial measurement units (IMU), infrared sensors, ultrasonic sensors, optical sensors, gyroscopes, magnetometers, odometers, pedometers, pressure sensors, strain gauges, GPS devices, a clock, etc.

Data collected by one or more wearable devices may be transmitted to the cloud or other remote server or device. Because each device may include several sensors collecting data continuously, or at a relatively high rate, the amount of data transmitted to the cloud may be voluminous. The transmitted raw data, by itself, may also be difficult to search or use.

SUMMARY

A wearable device may collect physiological data from a wearer of the device and transmit that data to the cloud or other remote server or device. A tag may be associated with all or part of the data based, at least in part, on an input by a wearer of the device. The input may be an indication of the state of the wearer, such as physical or mental state, or it may be a rule. Additional data associated with the wearer may also be synchronously collected by the system, such as personal (e.g., age, sex, occupation), motion (e.g., type of movement, speed, acceleration), and contextual (e.g., location, ambient temperature, time of day) data, and associated with tag. The collected data may be organized based on the tag and, in some examples, stored in a database. Data may also be collected from a population of wearers of the devices.

Some embodiments of the present disclosure provide a method including: (1) receiving, by a server from a wearable device, physiological data detected by a wearable device, wherein the wearable device is configured to be mounted to a body surface of a wearer; (2) receiving, by the server, an input from the wearer; (3) associating, by the server, all or part of the physiological data with a tag based, at least in part, on the input from the wearer; and (4) organizing, by the server, the physiological data based, at least in part, on the tag.

Further embodiments of the present disclosure provide a method including: (1) receiving, by a server, physiological data detected by a wearable device; (2) receiving, by the server, an input from a wearer of the wearable device; (3) associating, by the server, all or part of the physiological data with a tag based, at least in part, on the input from the wearer of the wearable device; (4) establishing, by the server, one or more groups based, at least in part, on the tag; and (5) storing, by the server, the physiological data in a database to indicate that all or part of the physiological data is a member of the one or more groups.

Still further embodiments of the present disclosure provide a method including: (1) receiving, by a server, initial physiological data from a wearable device; (2) receiving, by the server, an input from a wearer of the wearable device; (3) applying, by the server, a tag to all or a portion of the initial physiological data based on the input from the wearer of the wearable device; (4) receiving, by the server, subsequent physiological data from the wearable device; and (5) determining, by the server, whether to apply the tag to all or a portion of the subsequent data.

These as well as other aspects, advantages, and alternatives, will become apparent to those of ordinary skill in the art by reading the following detailed description, with reference where appropriate to the accompanying drawings.

DETAILED DESCRIPTION

Figure 1:
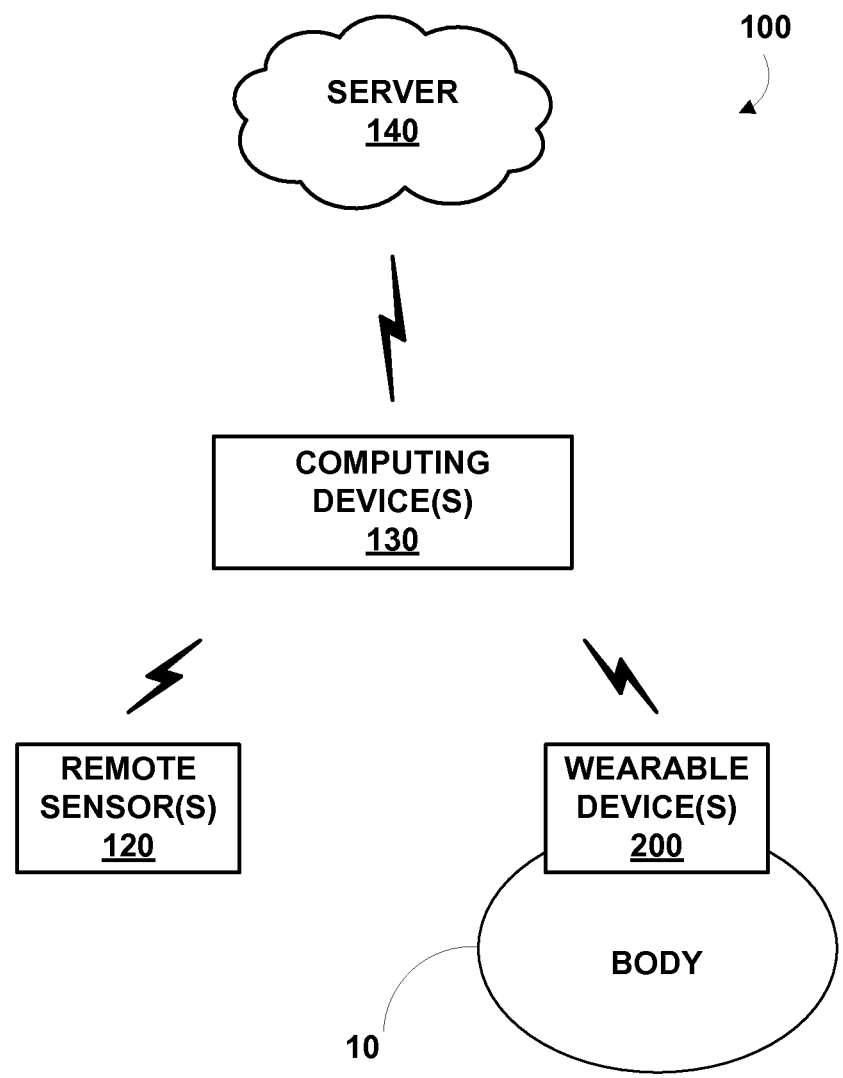
FIG. 1 is a block diagram of an example system that includes a wearable device, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may collect physiological and other data from a wearer of the device and transmit that data to the cloud or other remote server or device. For example, the wearable device may detect one or more physiological parameters, such as heart rate, blood pressure, respiration rate, blood oxygen saturation (SpO$_2$), skin temperature, skin color, galvanic skin response (GSR), muscle movement, eye movement, blinking, and speech. Some physiological data may also be obtained by non-invasively detecting and/or measuring one or more analytes present in blood, saliva, tear fluid, or other body fluid of the wearer of the device. The one or more analytes could include enzymes, reagents, hormones, proteins, viruses, bacteria, cells or other molecules, such as carbohydrates, e.g., glucose. Further, the wearable device, or a device associated with the wearable device, may collect motion-related data, such as the wearer's speed of travel, altitude, acceleration, cadence of movement, intensity of movement, direction of travel, orientation, gravitational force, inertia, and rotation. This data may be collected by sensors such as accelerometers, IMUs, proximity sensors, microphones, gyroscopes, magnetometers, optical sensors, ultrasonic sensors, odometers, and pedometers. Additionally, the wearable device may collect certain contextual data, such as a wearer's location, ambient light intensity, ambient temperature, time of day, a wearer's mode of travel, and a type of activity a wearer is participating in. Accordingly, the wearable device may include a location-tracking sensor (e.g., a GPS device), a light intensity sensor, a thermometer, and a clock. A wearer's personal or demographic data, such as sex, race, region or country of origin, age, weight, height, employment, medical history, etc., may also be collected and transmitted to the cloud.

The term "wearable device," as used in this disclosure, refers to any device that is capable of being worn or mounted at, on, in or in proximity to a body surface, such as a wrist, ankle, waist, chest, ear, eye, head or other body part. As such, the wearable device can collect data while in contact with or proximate to the body. For example, the wearable device can be configured to be part of a contact lens, a wristwatch, a "head-mountable display" (HMD), an orally-mountable device such as a retainer or orthodontic braces, a headband, a pair of eyeglasses, jewelry (e.g., earrings, ring, bracelet), a head cover such as a hat or cap, a belt, an earpiece, other clothing (e.g., a scarf), and/or other devices. Further, the wearable device may be mounted directly to a portion of the body with an adhesive substrate, for example, in the form of a patch, or may be implanted in the body, such as in the skin or another organ.

In some examples, the data described above may be collected directly by sensors integrated on the wearable device. Alternatively, or additionally, some or all of the data described above may be collected by sensors placed on other portions of a wearer's body or in communication with the body, other computing devices remote to the wearable device (such as a remote device having location tracking and internet capabilities, e.g. a smartphone, tablet or head-mountable device), or by manual input by the wearer. For example, the wearer may manually input when she is exercising, eating, work, or sleeping, the type of activity she is engaged in (running, typing, walking, climbing), her self-evaluated physical, health or mental state or mood (e.g., hungry, tired, headache, anxious, etc.), among other things. Data may also be collected from applications on other computing devices linked with the wearable device such as an electronic calendar, social media applications, restaurant reservation applications, travel applications, etc.

The wearable device (or remote device, the cloud, remote server, etc.) may be configured to automatically tag certain data collected from a wearer based on preset rules. The rules may include certain threshold levels, or other identifiable characteristics of the data that are known to be associated with the particular tag. The system would be configured to look for data meeting those characteristics and automatically apply a tag to that data. For example, the system may be configured to automatically apply a "sleeping" tag when some data or combination of data streams, such as heart rate, respiration rate and eye movement data, fall within certain ranges or exhibit certain characteristics. Additionally, the system may be configured to automatically apply a tag based on rules set by the wearer of the device or by a physician or other third party. In some examples, the wearer may desire to set certain goals, restrictions or thresholds on certain activities or habits, such as daily caloric intake, number of hours spent sedentary, daily water intake, etc. Rules may be set in the system to automatically tag data when goals are met or thresholds are exceeded.

The system may also be configured to receive an input from wearer of the device to tag a data point or segment of data. For example, the wearer of the device may indicate that she was sleeping from 10 PM to 6 AM and apply a "sleeping" tag to data collected during that time. The wearer may indicate a particular activity that she was previously engaged in for a certain period of time (e.g., exercising for 30 minutes), is presently engaged in (e.g., "working until 5 PM") or an activity that she anticipates being engaged in at a future time (e.g., "travelling by airplane from 8-11 AM"). The system may be configured to tag the data collected during the relevant time periods with the activity engaged in by the wearer of the device. These activities may be broken down into many categories and subcategories. For example, while "working" a wearer could also indicate whether he or she was sitting at her desk, at a meeting with a client or superior, taking on the phone, typing, etc. As described above, the system may also accept other inputs from the wearer about his or her physical state or mood. Many other annotations are contemplated.

Moreover, the wearable device, remote device, the cloud, or remote server may use supervised or machine learning to automatically determine when a tag should be applied to a data point or set of data. Once a wearer of a device identifies a data point or set of data as being associated with a particular tag, the system may be configured to "learn" or recognize other data that could be associated with that tag without the need for the wearer's manual input. In a first instance where a wearer selects a tag to be applied to incoming data, the wearable device may be configured to take high resolution data during that time period to assist in the learning process.

Tags, such as labels or annotations, may be applied to individual data points, or to sets of data. For example, if a wearer inputs into the wearable device or connected computing device that she is hungry, a "snapshot" of all data collected at that instantaneous time may be associated with the "hungry" tag. The system may be configured with certain preset tags that may be chosen by a wearer, or automatically applied to data. Such preset tags may make data aggregation more consistent and reliable and may include any category, metric or classification that may be deemed useful or interesting to a person viewing the data. Additionally, or alternatively, the system may be configured to allow the wearer to formulate or choose original tags.

All of the data collected by or input into the wearable device and any remote devices, and any tags applied thereto, may be time-synchronized and sent to the cloud. For example, if a wearer indicates that she is running, all data synchronously collected by the wearable device or any remote device should be tagged, for example, as "running" or "exercise" relevant data. The usability and searchability of the data collected and stored in the cloud may be increased by data tagging. Tags may be used by those viewing the data, such as a wearer, clinicians, physicians or marketing firms, to easily search for and collect relevant data points. In addition, tagging may assist in prioritizing analysis of data.

In particular, tags may make it possible to access and process large amounts of data quickly and easily, without having to search through a database for a particular type of data. Data may be organized based on the tags, such as, by aggregating all data having a common tag, e.g. the average number of hours all wearers slept in the past week. Tags may be used to recognize correlations or identify causation between data and the category of the tag. These correlations may be for an individual wearer or for a population of wearers and may be used to diagnose a present medical condition in a wearer of the device, or to predict the possible occurrence of a medical condition in the future. Tags may also be used by the system to assist a wearer in viewing, organizing or understanding her own data. For example, the tags may be used to compute performance or health statistics, such as the number of days the wearer jogged per week, and may assist a wearer in assessing set goals, such as the number of days she stayed below her caloric intake goal. Tags may also enable a wearer to compare her data to that of others having a common or similar tag. The tags may also be used to make recommendations to wearers. For example, processors in the cloud or remote server may analyze the data and identify trends, correlations, patterns, milestone events, etc., and recommend certain actions, products, remedies, etc. to the wearer of the device.

The term "medical condition" as used herein should be understood broadly to include any disease, illness, disorder, injury, condition or impairment—e.g., physiologic, psychological, cardiac, vascular, orthopedic, visual, speech, or hearing—or any situation affecting the health of the wearer of the device or requiring medical attention. A "medical condition" may also include a situation where a physiological parameter falls outside of a range, regimen or recommendation set by an individual, her physician, a clinician or a nutritionist. For example, a "medical condition" may be indicated when an individual consumes more than the daily recommended calories or consumes food having a high level of fat or sugars.

It should be understood that the above embodiments, and other embodiments described herein, are provided for explanatory purposes, and are not intended to be limiting.

II. Example Wearable Devices and Systems

A system 100, including one or more wearable devices 200 configured to be mounted to or worn on, in or in proximity to a body 10, one or more remote sensors 120, and one or more computing devices 130 all in communication with a server 140, is shown in FIG. 1. Remote sensor 120 may be any sensor not provided directly on the wearable device 200. For example, a remote sensor 120 may be mounted to a wearer's bicycle or car, on the wearer's desk, near a wearer's bed or outside of a wearer's home. Computing device 130 may be any device having computing or internet capabilities, including a smartphone or tablet, a personal computer, a mobile or cellular telephone, or a web-based application. In one embodiment, the one or more remote sensors 120 and wearable devices 200 indirectly communicate with server 140 via computing device 130. In other embodiments, the wearable device 200, remote sensor 120 and computing device 130 may all directly communicate with the server 140.

The device 200, remote sensor 120 and/or computing device 130 may be capable of collecting, detecting or measuring a plurality of parameters from or associated with a person wearing the device, such as physiological, motion, contextual, and personal parameters. As will be described further below, these parameters may be detected on one or more of the wearable device 200, the remote sensors 120 and the computing devices 130. Physiological parameters may include heart rate, blood pressure, respiration rate, blood oxygen saturation ($SpO_2$), skin temperature, skin color, galvanic skin response (GSR), perspiration, muscle movement, eye movement, blinking, speech and analyte concentration. Motion-related parameters, such as the wearer's speed of travel, altitude, acceleration, cadence of movement, intensity of movement, direction of travel, orientation, gravitational force, inertia, and rotation. Contextual parameters, such as a wearer's location, ambient light intensity, ambient temperature, humidity, allergen levels, pollution, time of day, a wearer's mode of travel, and a type of activity a wearer is participating in, may also be collected. A wearer's "location" could be any location with respect to a 2-dimensional or 3-dimensional coordinate system (e.g., a location with respect to X, Y and Z axes) or with respect to a cartographic location description (e.g., a street address), and may further include a global position (e.g., latitude, longitude and elevation), a hyper-local position (such as a location within a home or building), and/or any position at any level of resolution therebetween. Personal parameters may include sex, race, region or country of origin, age, weight, height, employment, occupation, and medical history, etc.

The wearable device 200, remote sensor(s) 120 and computing device(s) 130 may be configured to transmit data, such as collected physiological, motion, contextual and personal parameter data via a communication interface over one or more communication networks to the remote server 140. The communication interface may include any means for the transfer of data, including both wired and wireless communications, such as a universal serial bus (USB) interface, a secure digital (SD) card interface, a plain old telephone service (POTS) network, a cellular network, a fiber network and a data network. In one embodiment, the communication interface includes a wireless transceiver for sending and receiving communications to and from the server. The wearable device 200, remote sensor(s) 120 and computing device(s) 130 may also be configured to communicate with one another via any communication means.

Further, the computing device 130 may be capable of accessing information on the internet, a wearer's electronic calendar, or from a software application. The computing device 130 may collect data regarding the wearer's schedule, appointments, and planned travel. In some cases, the computing device 130 may also access the internet or other software applications, such as those operating on a wearer's smartphone. For example, the computing device 130 may access an application to determine the temperature, weather and environmental conditions at the wearer's location. Moreover, the computing device 130 may access a wearer's social media applications, such as Facebook, Foursquare or Twitter, to determine restaurants, stores or other locations a wearer has visited. This data may, for example, be relevant to correlating a wearer's reported illness with a restaurant she ate at. All of this collected data may be transmitted to the remote server 140.

In addition to receiving data from the wearable device 200, remote sensor(s) 120 and computing device(s) 130, the server may also be configured to gather and/or receive additional information from other sources. For example, the server may be configured to regularly receive viral illness or food poisoning outbreak data from the Centers for Disease Control (CDC) and weather, pollution and allergen data from the National Weather Service. Further, the server may be configured to receive data regarding a wearer's health state or existing medical conditions from a hospital or physician. Such information may be used in the server's decision-making process, such as recognizing correlations and in generating recommendations.

One or more of the wearable device 200, remote sensor 120 or computing device 130 may also be capable of receiving an input from a wearer and transmitting that input to the server 140. For example, the wearer may input one or more rules or an indication of her "state." As will be described further below, the wearable device 200 may include an interface 280 with one or more controls 284 via which the wearer may provide an input. A wearer may also provide an input on a computing device 130, such as a smartphone, tablet or laptop computer.

Figure 2:
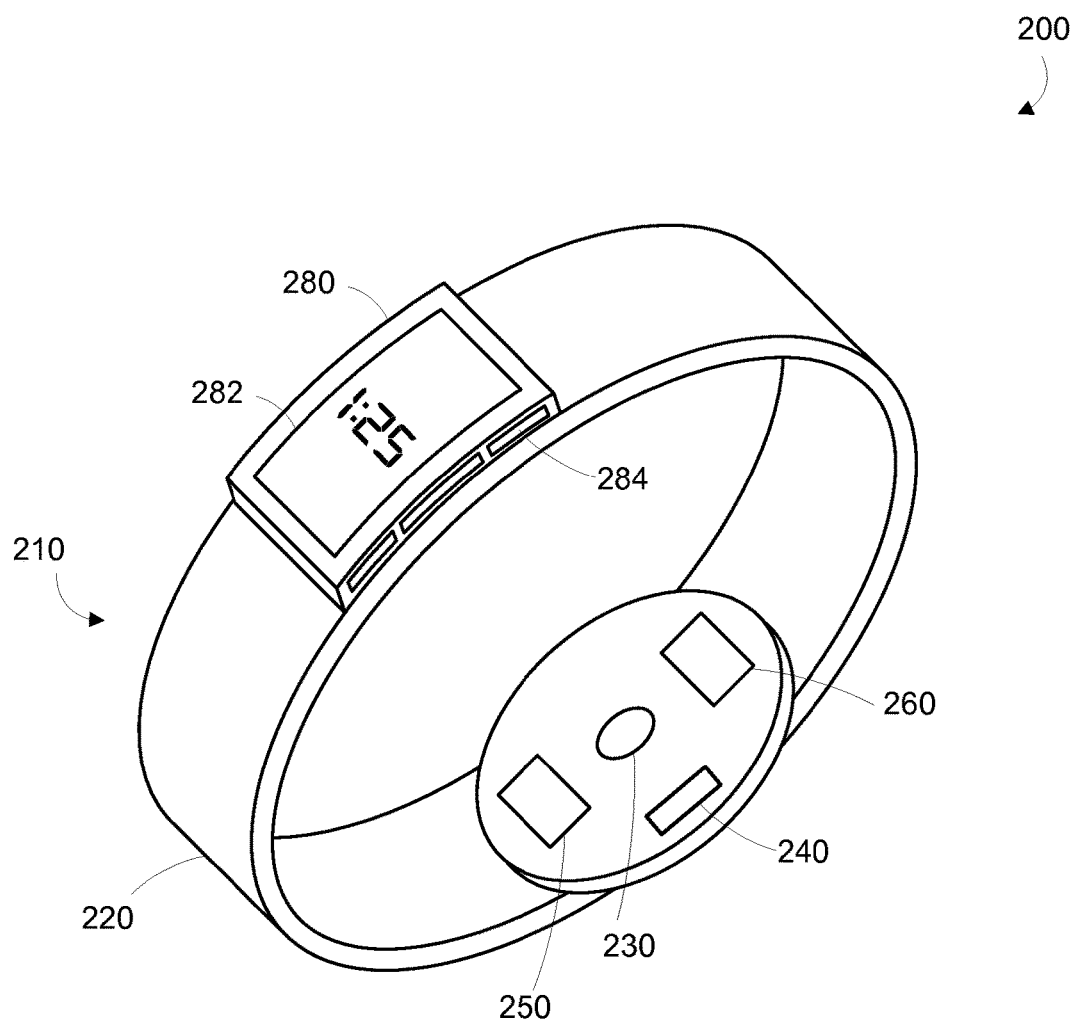
FIG. 2 illustrates an example of a wearable device.

Turning to FIG. 2, the wearable device 200 may be provided as any device configured to be mounted in, on or adjacent to a body surface. In the example shown in FIG. 2, the wearable device 200 is a wrist-mountable device 210, but many other forms are contemplated. The device may be placed in close proximity to the skin or tissue, but need not be touching or in intimate contact therewith. A mount 220, such as a belt, wristband, ankle band, necklace, or adhesive substrate, etc. can be provided to mount the device at, on or in proximity to the body surface.

The wearable device 200 may include one or more sensors 230 for collecting data from or associated with a wearer of the device 210, a transceiver 240 for transmitting collected data to a remote server or device, a processor 250 and a memory 260. Transceiver 240 may include a wireless transceiver with an antenna that is capable of sending and receiving information to and from a remote source, such as a server 140. Memory 260 is a non-transitory computer-readable medium that can include, without limitation, magnetic disks, optical disks, organic memory, and/or any other volatile (e.g. RAM) or non-volatile (e.g. ROM) storage system readable by the processor 250. The memory 260 can include a data storage to store indications of data, such as sensor readings, program settings (e.g., to adjust behavior of the wearable device 200), user inputs (e.g., from a user interface on the device 200 or communicated from a remote device), etc. The memory 260 can also include program instructions for execution by the processor 250 to cause the device 200 to perform processes specified by the instructions. Example processor(s) 250 include, but are not limited to, CPUs, Graphics Processing Units (GPUs), digital signal processors (DSPs), application specific integrated circuits (ASICs).

The sensors 230 may include any device for collecting, detecting or measuring one or more physiological, motion, contextual or personal parameters. Sensors for detecting and measuring physiological parameters may include, but are not limited to, one or more of an optical (e.g., CMOS, CCD, photodiode), acoustic (e.g., piezoelectric, piezoceramic), electrochemical (voltage, impedance), resistive, thermal, mechanical (e.g., pressure, strain), magnetic, or electromagnetic (e.g., magnetic resonance) sensor. In particular, the wearable device 100 may include sensors such as a thermometer and a GSR sensor for sensing temperature and skin resistance, respectively, and a light emitting source and a detector for sensing blood pressure. Some physiological data may also be obtained by non-invasively detecting and/or measuring one or more analytes present in blood, saliva, tear fluid, or other body fluid of the wearer of the device. The one or more analytes could include enzymes, reagents, hormones, proteins, viruses, bacteria, cells or other molecules, such as carbohydrates, e.g., glucose. Analyte detection and measurement may be enabled through several possible mechanisms, including electrochemical reactions, change in impedance, voltage, or current etc. across a working electrode, and/or interaction with a targeted bioreceptor. For example, analytes in a body fluid may be detected or measured with one or more electrochemical sensors configured to cause an analyte to undergo an electrochemical reaction (e.g., a reduction and/or oxidation reaction) at a working electrode, one or more biosensors configured to detect an interaction of the target analyte with a bioreceptor sensitive to that analyte (such as proteins, enzymes, reagents, nucleic acids, phages, lectins, antibodies, aptamers, etc.), and one or more impedimetric biosensors configured to measure analyte concentrations at the surface of an electrode sensor by measuring change in impedance across the electrode, etc. Other detection and quantification systems and schemes are contemplated for implementation of the analyte sensor system.

Contextual parameters may be detected from, for example, a location-tracking sensor (e.g., a GPS or other positioning device), a light intensity sensor, a thermometer, a microphone and a clock. Motion data may be collected by sensors such as accelerometers, IMUs, proximity sensors, microphones, gyroscopes, magnetometers, optical sensors, ultrasonic sensors, odometers, and pedometers. These sensors and their components may be miniaturized so that the wearable device may be worn on the body without significantly interfering with the wearer's usual activities. Additionally or alternatively, these sensors may be provided on or as part of a remote sensor 120 or a computing device 130.

The wearable device 200 may also include an interface 280 via which the wearer of the device may receive one or more recommendations or alerts generated either from a remote server 140, remote computing device 130, or from the processor 250 provided on the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the interface 280 may include a display 282 where a visual indication of the alert or recommendation may be displayed. The display 282 may further be configured to provide an indication of the detected or collected physiological, motion, contextual or personal parameters, for instance, the wearer's heart rate. In embodiments where the wearable device is not capable of supporting an interface 280, alerts and recommendations may be provided to the wearer on computing device 130. The interface 280 may also include one or more controls 284 via which a user may input an indication of her state, or, in some cases a rule related to the data detected by the wearable device.

In other examples, the wearable device 200 may be provided as or include an eye-mountable device, a head mountable device (HMD) or an orally-mountable device. An eye-mountable device may, in some examples, take the form of a vision correction and/or cosmetic contact lens, having a concave surface suitable to fit over a corneal surface of an eye and an opposing convex surface that does not interfere with eyelid motion while the device is mounted to the eye. The eye-mountable device may include at least one sensor provided on a surface of or embedded in the lens material for collecting data. In one example, the sensor can be an amperometric electrochemical sensor for sensing one or more analytes present in tear fluid.

An HMD may generally be any display device that is capable of being worn on the head and places a display in front of one or both eyes of the wearer. Such displays may occupy a wearer's entire field of view, or occupy only a portion of a wearer's field of view. Further, head-mounted displays may vary in size, taking a smaller form such as a glasses-style display or a larger form such as a helmet or eyeglasses, for example. The HMD may include one or more sensors positioned thereon that may contact or be in close proximity to the body of the wearer. The sensor may include a gyroscope, an accelerometer, a magnetometer, a light sensor, an infrared sensor, and/or a microphone for collecting data from or associated with a wearer. Other sensing devices may be included in addition or in the alternative to the sensors that are specifically identified herein.

An orally mountable device may be any device that is capable of being mounted, affixed, implanted or otherwise worn in the mouth, such as on, in or in proximity to a tooth, the tongue, a cheek, the palate, the lips, the upper or lower jaw, the gums, or other surface in the mouth. For example, the device 200 can be realized in a plurality of forms including, but not limited to, a crown, a retainer, dentures, orthodontic braces, dental implant, intra-tooth device, veneer, intradental device, mucosal implant, sublingual implant, gingivae implant, frenulum implant, or the like. The orally-mountable device may include one or more sensors to detect and/or measure analyte concentrations in substances in the mouth, including food, drink and saliva. Sensor(s) that measure light, temperature, blood pressure, pulse rate, respiration rate, air flow, and/or physiological parameters other than analyte concentration(s) can also be included.

Some embodiments of the system 100 and/or wearable devices 200 may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a wearer's identity may be treated so that no personally identifiable information can be determined for the wearer, or a wearer's geographic location may be generalized where location information is obtained (such as to a city, ZIP code, or state level), so that a particular location of a wearer cannot be determined.

Additionally or alternatively, wearers of a device may be provided with an opportunity to control whether or how the device collects information about the wearer (e.g., information about a wearer's medical history, social actions or activities, profession, a wearer's preferences, or a wearer's current location), or to control how such information may be used. Thus, the wearer may have control over how information is collected about him or her and used by a clinician or physician or other wearer of the data. For example, a wearer may elect that data, such as health state and physiological parameters, collected from his or her device may only be shared with certain parties or used in certain ways.

III. Example Methods

Figure 3:
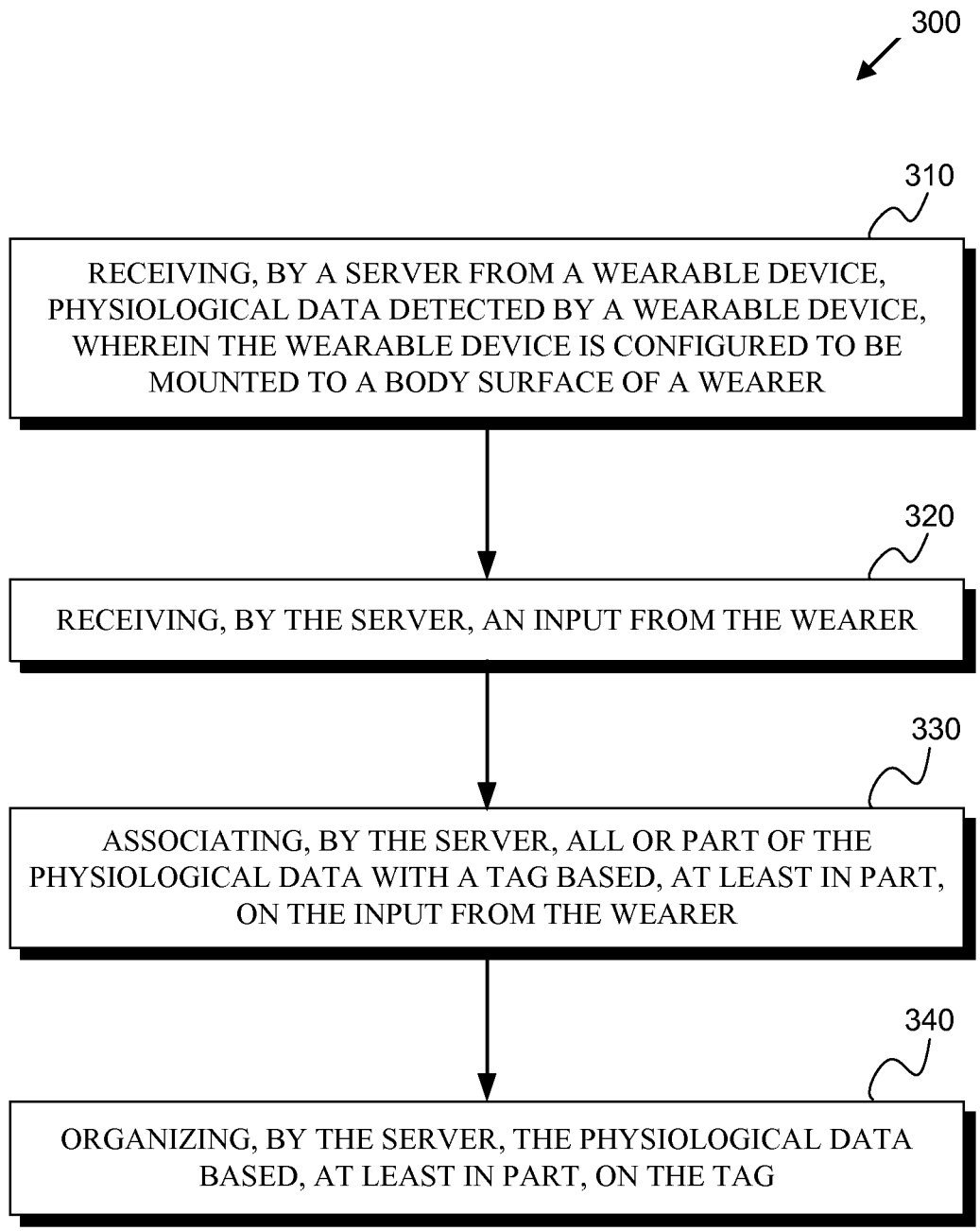
FIG. 3 is a flow chart of an example method, according to an example embodiment.

FIG. 3 is a flowchart of a method 300 for tagging data detected from a wearer of a wearable device. As described above, a wearable device 200, configured to be mounted to a body surface, may detect physiological data from a wearer of the device. This detected data may then be received by, for example, a processor on the wearable device 200, a remote computing device 130 or a remote server 140, such as a cloud computing network (310). An input by the wearer of the device may also be received, for example, by the server 140 (320). The input may be received directly by the server 140, or may be input by the wearer into the wearable device 200, a remote sensor 120, or a computing device 130, such as a smartphone or laptop computer and transmitted to the server 140. While embodiments of the foregoing methods are described herein as being carried out on the server 140, it is contemplated that the methods may be carried out by a processor on the wearable device 200, remote sensor 120 or computing device 130.

In one example, the wearer may input her "state", which may include any type of activity the wearer is engaged in, a task being performed by the wearer, and the wearer's a health state, physical state, mental state and mood. For example, the wearer may indicate that she is at work, standing, sleeping, making dinner, or exercising. A wearer may also input how she is feeling or any symptoms he or she is experiencing, such as, "feeling cold," "feeling tired," "stressed," "feeling rested and energetic," "hard to breathe," etc. More than one state may also be input at a time. In some examples, the wearer may concurrently input a state and one or more specific sub-states, such as, "at work" and "typing" or "at the gym" and "lifting weights." In other examples, the wearer may concurrently input different types of states, such as, "at work" and "feeling tired." Further, the wearer may input that the state applies to a period of time, for example, a wearer may input that she was at work between 9 am and 5 pm, or that she was running from 6 am to 6:45 am. The system may also be configured with a stopwatch or timer function where a wearer may input when a state is initiated and input when the state ends.

In another example, the input may be a rule set by the wearer of the device. The wearer may input rules against which future data may be compared. For example, the wearer may specify that she swims for 30 minutes at the gym every Tuesday starting at 12 pm or that she is at work between 9 am and 5 pm every weekday. The rule may be based in some embodiments on a threshold, such as, a maximum or minimum recommended caloric intake or a heart rate range for aerobic exercise. The rule may also be related to a goal of the wearer of the wearable device, such as a number of times the wearer aims to run in a week or the number of hours of sleep a wearer aims to sleep each night.

Based on the wearer's input, all or part of the physiological data may be associated with a tag by the server 140 (330). The tag may be any word, phrase, expression, or symbol that can be used to label all or part of the physiological data. In some examples, the wearer's input may be used, at least in part, to generate the tag. For example, the wearer may input that she was sleeping between 10 pm and 6 am and a "sleeping" tag may be generated and applied to data collected between 10 pm and 6 am. The generated tag may then be saved in the system and selected by the wearer on another occasion. Tags may be associated with physiological data synchronously with its collection, or they may be applied at some time after data has been collected. If the wearer inputs that she is beginning a run, then all data collected from that point in time until the wearer inputs that her run has ended will be associated with, for example, a "running" tag. Alternatively, the wearer may input after completion of an activity that, for example, she was sitting for the last thirty minutes or that she experienced a headache yesterday at noon.

In other examples, where the wearer's input is a rule, all or part of the collected physiological data may be associated with a tag based on the rule. According to one example described above, where the wearer inputs a rule that she swims for 30 minutes at the gym every Tuesday starting at 12 pm, a "swimming" tag may be applied to all data collected between 12 pm and 12:30 pm every Tuesday. Where, for example, the rule is based on a threshold, a tag may be applied to collected data that falls above or below that threshold, or outside of a range. Further, where the rule is based on a goal set by the wearer, collected data may be compared to the rule and tagged, for example, as "goal met," "goal exceeded," or "goal not met."

The physiological data may be organized by the server based, at least in part, on the tag associated with the collected data (340). In one example, the physiological data may be organized by aggregating a plurality of physiological data detected from the wearer of a wearable device associated with that tag. The data may be organized by aggregating all of a wearer's data that is associated with a "sleeping" tag. Similarly, data may be organized by aggregating all data that is associated with two tags, such as, "consumed bread" and "stomach ache." Further, data associated with a tag may be organized by time of day, day of the week, and value. For example, data tagged with "sleeping" may be organized by the number of hours of sleep or the time of day sleep started or ended. Data may also be organized by related tags, for example all data tagged with "sleeping" may be organized with data tagged with "snoring." Many other organization schemes are contemplated.

Figure 4:
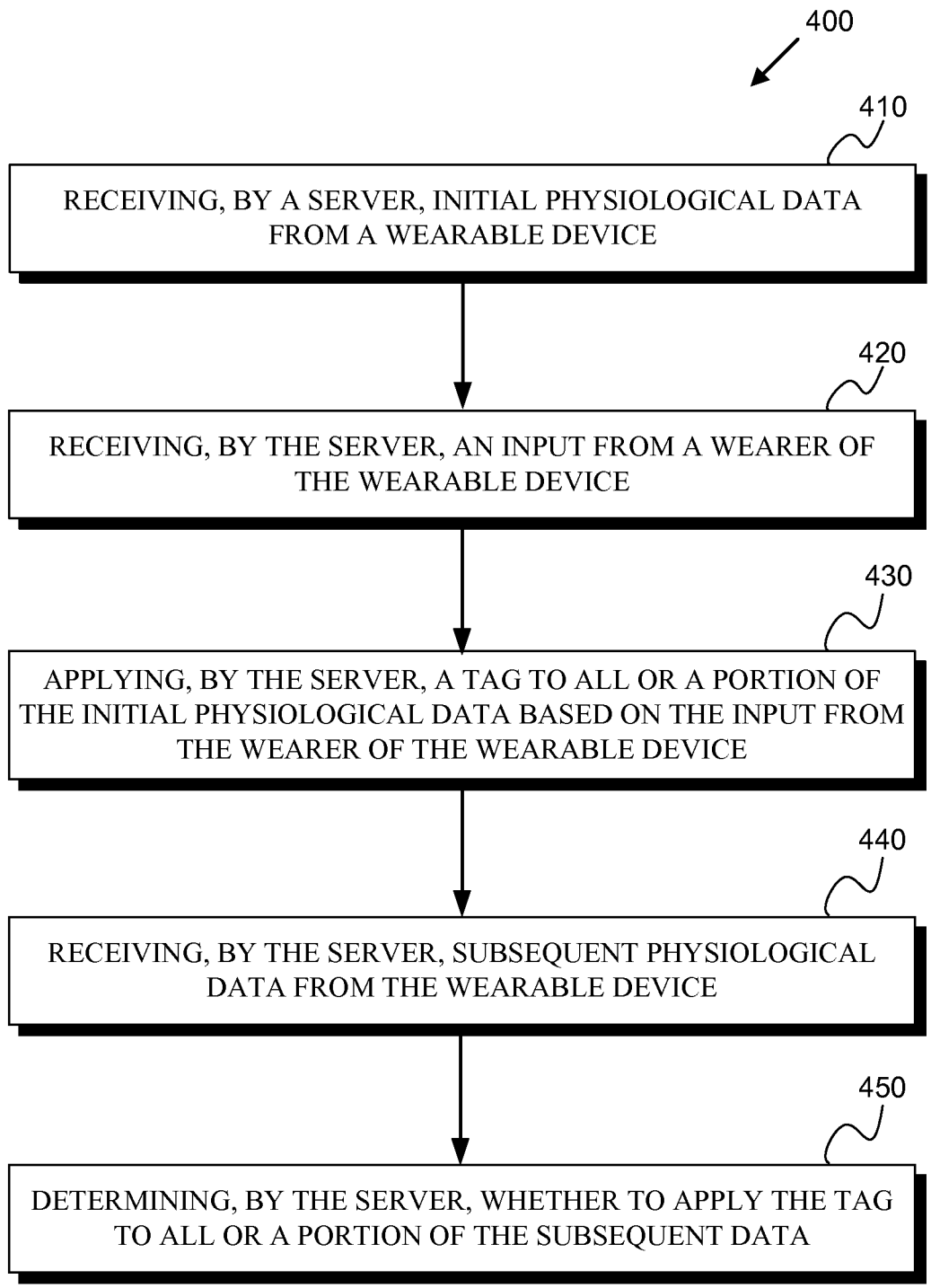
FIG. 4 is a flow chart of an example method, according to an example embodiment.

In some embodiments, tags may also be applied to data based on learned rules. FIG. 4 illustrates a flow chart for an additional method 400. Initial physiological data is received by the server from a wearable device (410). The server also receives an input from the wearer of the wearable device (420) and applies a tag to all or a portion of that initial data based on the input received from the wearer (430). Subsequent physiological data is received by the server from the wearable device (440) and the server, or other computing device, determines whether to apply the tag to all or a portion of the subsequent data (450). In some examples, the subsequent data may be automatically associated with a tag based on a learned rule which may be based, at least in part, on a comparison between some physiological data is associated with a tag and subsequently received physiological data. The server 140 or other computing device in the system 100 may be configured to use supervised or machine learning to determine when a tag should be applied to a data point or set of data based on the type of data a particular tag was previously associated with. Once a data point or set of data is associated with a particular tag based on a wearer's initial input, the system may be configured to "learn" or recognize other data that could be associated with that tag without the need for a subsequent input by the wearer. The system may recognize patterns and generate rules based on these patterns. For example, the system may recognize that on a certain number of instances where a wearer input that she was sleeping, the wearer's heart rate and respiration rate always fell within a certain range for that period of time. Accordingly, when subsequent heart rate and respiration data within that identified range is received, the system may automatically apply a "sleeping" tag to that data without the wearer having to input that she was sleeping. This machine or supervised learning may be facilitated by taking high resolution data during a time period where a wearer inputs a tag for the first time.

Learned rules may also be based, at least in part, on an input by the wearer of the device. In some cases, a wearer may provide an input into the system to "correct" a learned rule. For example, the system may create a learned rule such that, whenever a wearer's data exhibits values A, B and C, then the data is associated with an "eating" tag. As described above, this learned rule may be based on an earlier input received by the wearer indicating that she was eating at a time when her collected data exhibited values A, B and C. The user may provide an input at a later that may correct the tag by (1) change the initial indication upon which the learned rule was based from, for example, "eating" to "drinking" or (2) by correcting certain instances of when the learned rule applied the "eating" tag. For example, the wearer may recognize that the learned rule incorrectly applied to the "eating" tag to data collected while she was, in fact, drinking. In some examples, the system may use this further input by the user to adjust the learned rule to distinguish between data collected during eating and data collected during drinking.

Further, physiological data associated with a plurality of wearers of respective wearable devices may be received by the server and associated with one or more tags. The tags may be associated with each wearer's data based, at least in part, on an input from that respective wearer received by the server. The data collected from this plurality of wearers may be organized by the server based on the one or more tags applied to their respective data. In some examples, the physiological data may be organized by aggregating physiological data associated with each of the plurality of wearers. Similar to that described above, data from any of the plurality of wearers that is associated with a particular tag may be aggregated together.

Physiological data collected from a plurality of wearers may also be used in the creation of learned rules. The system may be configured to "learn" or recognize data collected from a wearer of the device that should be associated with a tag based on a comparison of that data to data collected from a population of wearers that is also associated with that tag. Accordingly, a learned rule for applying a tag to a wearer's data may also be based on a comparison of that wearer's physiological data to data collected from a plurality of wearers that is also associated with that tag. In some cases, comparing a wearer's data to data collected from a plurality of wearers may improve the accuracy of these learned rules. For example, the system may be more able to determine when a wearer is engaging in a particular activity (e.g., bungee jumping) when it can compare the wearer's data to a plurality of other data sets that are tagged with that activity.

In addition to physiological data, the server 140 may be configured to receive motion data, contextual data, and personal data associated with the wearer of a wearable device. As described above, these types of data may be detected or collected by one or more of a wearable device 200, a computing device 130, a remote sensor 120 or the server 140. The motion and contextual data may be detected synchronously with the physiological data. Time synchronization data may also be received by the server 140 that indicates a timing relationship between the physiological and the motion and/or contextual data. By time synchronizing the data, the same tag may be applied to all physiological, motion and contextual data that is detected at the same time. A wearer's personal data may also be associated with the other forms of data and may, in some examples, be used with the tag to organize the data. Data collected from a population of wearers may be organized based on a common tag and one or more personal data parameters, such as height, weight, gender, sex, home address, occupation, etc.

For example, data collected from women between the ages of 30 and 34 and tagged with "running" may be organized together.

Figure 5:
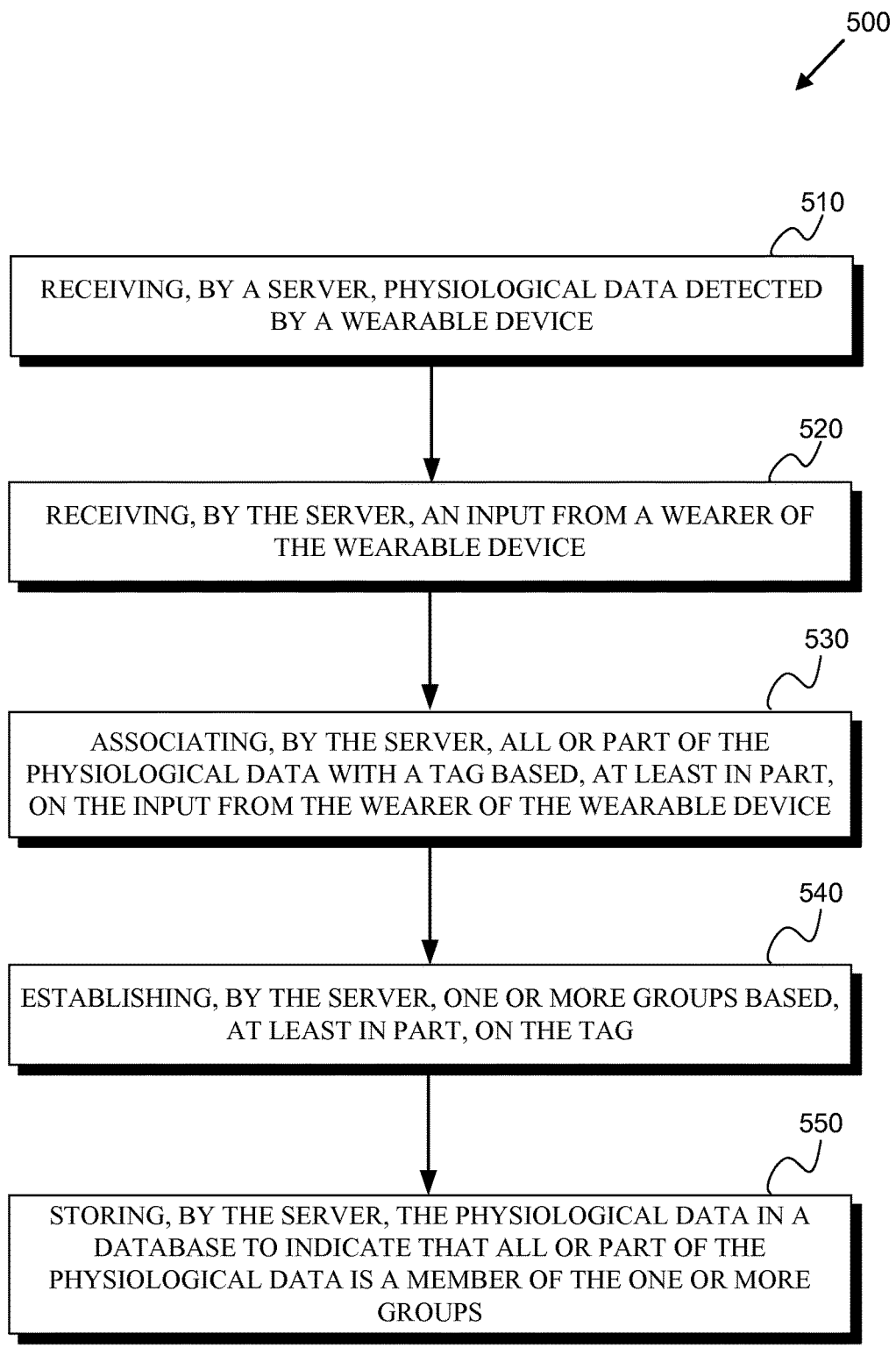
FIG. 5 is a flow chart of an example method, according to an example embodiment.

Another method 500 is illustrated in the flowchart of FIG. 5. Physiological data detected by a wearable device is received by a server (510) along with an input from the wearer of the wearable device (520). All or part of the physiological data is associated by the server with a tag based, at least in part, on the input from a wearer of the wearable device (530), similar to that described above with respect to method 300. Based on the tag, one or more groups are established by the server (540) and the physiological data is stored by the server in a database to indicate that all or part of the physiological data is a member of the one or more groups (550). In addition to being based on the tag, the one or more groups established in the database may also be based on personal data of a wearer of the device. For example, "running" group may be established within the database for women over the age of 50 and all data with a common tag and having those personal data characteristics would be stored within the database to indicate that the physiological data associated with that tag was a member of the group. Further, a wearer's time-synchronized contextual and motion data may also be stored in the database with the corresponding physiological data to indicate that all or part of the contextual or motion data is a member of the group.

Tags may be used to organize data stored in the server 140 to increase its usability and searchability. Tags may be used by the wearer in viewing and using her data or by third parties who have been given permission by the wearer, such as clinicians or physicians. In one example, tags may provide a convenient means to query a database in which a wearer or population of wearers' data is stored or to conveniently view large amounts of data in an organized fashion. Tags may be used aggregate similar data points or data sets from a plurality of wearers or from a single wearer over time. The tags may also provide a means for organizing many different types of data, such as physiological, contextual, motion and personal data. To this end, data may be aggregated based on one or more tags and one or more different types of data. In addition, tagging may assist in prioritizing analysis of data, for example, all data tagged as being above a threshold may be reviewed first.

Tags may be used to recognize correlations or identify causation between data and the category of the tag. These correlations may be for an individual wearer or for a population of wearers and may be used to diagnose a present medical condition in a wearer of the device, or to predict the possible occurrence of a medical condition in the future. In addition, the tags may be used to see change or stability of data over time, for example, how a wearer's average resting heart rate changed over a three month period. Tags may be used to determine the effect that a tagged activity had on physiological data, such as the effect running had on a wearer's heart rate.

Correlations may be derived between physiological data measured a wearable device and a tag, which may have been generated by the health state input by the wearer, and all other information collected by the server or other computing device also associated with that tag. For example, analysis of physiological data associated with a tag (which may represent a wearer's input health state) may reveal that the patient reported experiencing certain adverse health conditions, such as a migraine or a heart attack, when one or more physiological parameters reach a certain level. This correlation data may be used to generate recommendations for the patient. Physiological data such as blood pressure, heart rate, body temperature etc., may be complemented by motion and contextual data, in order to add to or enhance these correlations. In this respect, tags may be particularly useful in drawing correlations between many different types of data sharing a common or similar tag. For example, the analysis of physiological data measured by the wearable device 200 and the location of the wearable device (which may, for example, be determined from a remote sensor 120) may reveal that the wearer of the device experiences certain adverse health conditions, such as allergic reaction, when present in a certain geographical region. Further, date, time of day and geographical location data may be used to detect and monitor spatial and temporal spreading of diseases among a population of wearers.

Further, tags may be used by a wearer to view and use her own data. For example, the tags may be used to compute performance statistics, such as the number of days the wearer jogged per week, or health statistics, such as the number of days the wearer spent on bed rest in the previous year. The tags may also be used by a wearer of the device to determine if she met certain set goals, such as the number of days the wearer stayed below her caloric intake goal. Tags may also be used by the wearer of a device to run any number of queries on her data, e.g., number of days experiencing hunger, number of days experiencing hunger and headache, nights REM sleep was achieved, etc. Further, the tags may be used by a wearer to compare her data to that of others. For example, the wearer may determine how her exercise level compares to that of others in her sex, age group, location, profession, etc.

The tags may also be used to make recommendations to wearers. For example, processors in the remote server 140 may analyze the data and identify trends, correlations, patterns, milestone events, etc., and recommend certain actions, products, remedies, etc. to the wearer of the device. For example, the server may recognize that data collected from a wearer on three different instances was tagged with "stomach ache" within a few hours after the wearer input that she consumed a wheat-based product. The server may then recommend that the wearer of the device see a doctor to discuss a potential gluten allergy. In another example, the server may recommend that a wearer exercise more if she did not engage in the recommended level of activity during a certain period. These recommendations may be based on, for example, generally recognized standards or norms, on approved drug indications, or on intended or recommended product uses. The recommendations may also be set or provided by a wearer's physician or caretaker. In other examples, the tags may be used for targeted marketing. In one example, the system may recommend a product or service based on one or more tags applied to a wearer's data, such as, a recommendation for a pain medication aid if the wearer tagged data indicating she experienced a headache.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A method, comprising:
   receiving, by a server from a wearable device, first physiological data detected by a wearable device, wherein the wearable device is configured to be mounted to a body surface of a wearer;
   receiving, by the server, an input from the wearer;
   associating, by the server, all or part of the first physiological data with a tag based, at least in part, on the input from the wearer;
   organizing, by the server, the first physiological data based, at least in part, on the tag;
   receiving, by the server from one or more other wearable devices, second physiological data related to one or more wearers of the one or more other wearable devices, wherein the second physiological data is associated with the tag;
   receiving, by the server from the wearable device, third physiological data detected by the wearable device;
   determining, by the server, a learned rule based, at least in part, on (i) a comparison of at least some of the third physiological data and the first physiological data associated with the tag and (ii) a comparison of at least some of the third physiological data and the second physiological data associated with the tag; and
   associating, by the server, all or part of the third physiological data with the tag based on the learned rule.

2. The method of claim 1, wherein the tag is generated based, at least in part, on the input from the wearer.

3. The method of claim 1, wherein the input is a state of the wearer.

4. The method of claim 3, wherein the state comprises one or more of: (a) a type of activity engaged in by the wearer, (b) a task performed by the wearer, (c) a health state of the wearer, (d) a physical state of the wearer, (e) a mental state of the wearer, or (f) a mood of the wearer.

5. The method of claim 1, wherein the input is a rule.

6. The method of claim 5, wherein the rule is based, at least in part, on a threshold value.

7. The method of claim 1, wherein the learned rule is further based, at least in part, on the input by the wearer.

8. The method of claim 1, wherein organizing the first physiological data comprises aggregating a plurality of physiological data detected from the wearer of the wearable device associated with the tag.

9. The method of claim 1, wherein the first physiological data comprises one or more of: (a) a heart rate, (b) a respiration rate, (c) a body temperature, or (d) a level of perspiration.

10. The method of claim 1, further comprising:
    associating, by the server, all or part of the second physiological data related to the one or more wearers of the one or more other wearable devices with the tag based, at least in part, on respective inputs from the one or more wearers; and
    organizing, by the server, the second physiological data based, at least in part, on the tag.

11. The method of claim 10, wherein organizing the second physiological data comprises aggregating the second physiological data related to the one or more wearers based on the tag.

12. The method of claim 1, further comprising:
    receiving, by the server, motion data associated with the wearer of the wearable device, wherein the motion data is detected synchronously with the first physiological data;
    receiving, by the server, time-synchronization data that indicates a timing relationship between the motion data and the first physiological data; and
    applying, by the server, the tag to the motion data based, at least in part, on the time-synchronization data.

13. The method of claim 12, wherein the motion data comprises one or more of: (a) a speed of travel, (b) an altitude, (c) an acceleration, (d) a cadence of movement, (e) an intensity of movement, (f) a direction of travel, (g) an orientation, (h) a gravitational force, (i) an inertia, or (j) a rotation.

14. The method of claim 1, further comprising:
    receiving, by the server, contextual data associated with the wearer of the wearable device, wherein the contextual data is detected synchronously with the first physiological data;
    receiving, by the server, time-synchronization data that indicates a timing relationship between the contextual data and the first physiological data; and
    applying, by the server, the tag to the contextual data based, at least in part, on the time-synchronization data.

15. The method of claim 14, wherein the contextual data comprises one or more of: (a) a location of the wearer of the device, (b) an ambient light intensity, (c) an ambient temperature, (c) a time of day, (d) a mode of travel of the wearer of the device, or (e) a type of activity the wearer of the device is engaged in.

16. The method of claim 1, further comprising:
    receiving, by the server, personal data associated with the wearer of the device; and
    organizing, by the server, the first physiological data, based, at least in part, on the tag and the personal data.

17. The method of claim 16, wherein the personal data comprises one or more of: (a) a height of the wearer of the device, (b) a weight of the wearer of the device, (c) an age of the wearer of the device; (d) a gender of the wearer of the device; (e) a race of the wearer of the device; (f) a medical history of the wearer of the device; or (g) an occupation of the wearer of the device.

18. The method of claim 1, wherein determining the learned rule comprises:
    identifying one or more patterns of the first physiological data and the second physiological data;
    determining that the third physiological data has the identified one or more patterns; and
    determining the learned rule based on the third physiological data having the identified one or more patterns.

19. The method of claim 1, wherein the tag comprises a label or annotation, and wherein associating all or part of the first physiological data with the tag comprises storing the first physiological data in a database and applying the label or annotation to all or part of the stored first physiological data.

20. A method, comprising:
    receiving, by a server, first physiological data detected by a wearable device;
    receiving, by the server, an input from a wearer of the wearable device;

associating, by the server, all or part of the first physiological data with a tag based, at least in part, on the input from the wearer of the wearable device;

establishing, by the server, one or more groups based, at least in part, on the tag;

storing, by the server, the first physiological data associated with the tag in a database to indicate that all or part of the first physiological data associated with the tag is a member of the one or more groups;

receiving, by the server from one or more other wearable devices, second physiological data related to one or more wearers of the one or more other wearable devices, wherein the second physiological data is associated with the tag;

storing, by the server, the second physiological data associated with the tag in the database to indicate that all or part of the second physiological data associated with the tag is a member of the one or more groups;

receiving, by the server from the wearable device, third physiological data detected by the wearable device;

determining, by the server, a learned rule based, at least in part, on (i) a comparison of at least some of the third physiological data and at least some of the first physiological data associated with the tag and (ii) a comparison of at least some of the third physiological data and at least some of the second physiological data associated with the tag;

associating, by the server, at least some of the third physiological data with the tag based on the learned rule; and storing, by the server, the third physiological data associated with the tag in the database to indicate that all or part of the third physiological data associated with the tag is a member of the one or more groups.

21. The method of claim 20, wherein the group is further based, at least in part, on personal data of the wearer of the device.

22. The method of claim 20, further comprising:

receiving, by the server, motion data associated with the wearer of the wearable device, wherein the motion data is detected synchronously with the first physiological data;

receiving, by the server, time-synchronization data that indicates a timing relationship between the motion data and the first physiological data;

associating, by the server, all or part of the motion data with the tag based, at least in part, on the time-synchronization data; and storing, by the server, the motion data in the database to indicate that all or part of the motion data is a member of the one or more groups.

23. The method of claim 20, further comprising:

receiving, by the server, contextual data associated with the wearer of the device, wherein the contextual data is detected synchronously with the first physiological data;

receiving, by the server, time-synchronization data that indicates a timing relationship between the contextual data and the first physiological data;

associating, by the server, all or part of the contextual data with the tag based, at least in part, on the time-synchronization data; and storing, by the server, the contextual data in the database to indicate that all or part of the contextual data is a member of the one or more groups.

24. A method, comprising:

receiving, by a server, first physiological data from a wearable device;

receiving, by the server, an input from a wearer of the wearable device;

applying, by the server, a tag to all or a portion of the first physiological data based on the input from the wearer of the wearable device;

receiving, by the server from one or more other wearable devices, second physiological data related to one or more wearers of the one or more other wearable devices, wherein the tag is applied to the second physiological data;

receiving, by the server, third physiological data from the wearable device;

determining, by the server, a learned rule based, at least in part, on (i) a comparison between at least some of the third physiological data and at least some of the first physiological data having the applied tag and (ii) a comparison of at least some of the third physiological data and at least some of the second physiological data having the applied tag; and determining, by the server, whether to apply the tag to all or a portion of the third physiological data based, at least in part, on the learned rule.

25. The method of claim 24, wherein the tag is generated based, at least in part, on the input from the wearer.

26. The method of claim 24, wherein the input is a state of the wearer, and wherein the state comprises one or more of: (a) a type of activity engaged in by the wearer, (b) a task performed by the wearer, (c) a health state of the wearer, (d) a physical state of the wearer, (e) a mental state of the wearer, or (f) a mood of the wearer.

* * * * *